United States Patent [19]

Edelman et al.

[11] 4,403,983
[45] Sep. 13, 1983

[54] DUAL LUMEN SUBCLAVIAN CANNULA

[75] Inventors: William Edelman, Long Beach; Michael Baranowski, Corona Del Mar, both of Calif.

[73] Assignee: Shiley Incorporated, Irvine, Calif.

[21] Appl. No.: 318,715

[22] Filed: Nov. 6, 1981

[51] Int. Cl.³ .............................................. A61M 25/00
[52] U.S. Cl. ...................................................... 604/43
[58] Field of Search ............. 128/214 R, 214.2, 214.4, 128/221, 348, 240; 604/27, 43, 164, 280

[56] References Cited

U.S. PATENT DOCUMENTS 2,564,977 8/1951 Hu ..................................... 128/221 X
4,134,402 1/1979 Mahurkar ........................ 128/214 R

FOREIGN PATENT DOCUMENTS 1092927 1/1981 Canada ................................. 128/348
592193 4/1925 France .............................. 128/214 R Primary Examiner—Dalton L. Truluck
Attorney, Agent, or Firm—Charles J. Knuth; Peter C. Richardson; Edward B. Cantey, Jr.

[57] ABSTRACT

A dual lumen subclavian cannula is disclosed for use in hemodialysis where the lumens are formed by a septum dividing an essentially circular tube longitudinally. The blood return lumen is closed at its distal end by a blunt point and has openings in its side wall proximal to the point. The blood inlet lumen has an open distal end plus openings in the side wall which are proximal to the analogous openings in the blood return lumen. A manifold at the proximal end of the tube separately distributes blood into the return lumen and collects blood from the inlet lumen.

6 Claims, 4 Drawing Figures

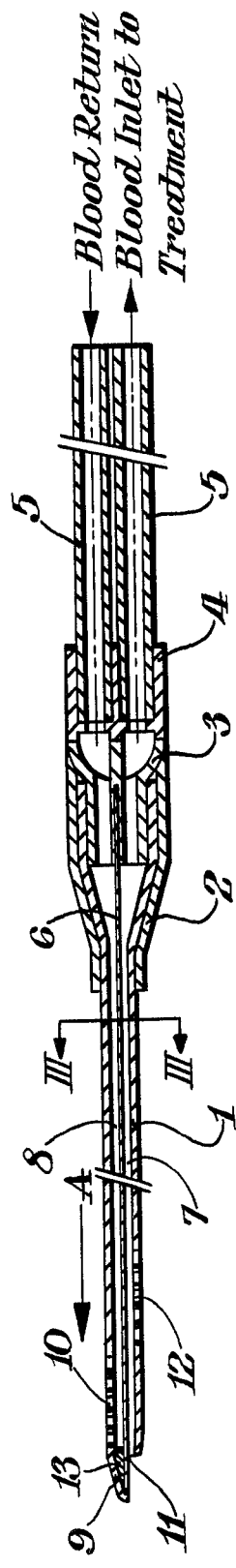
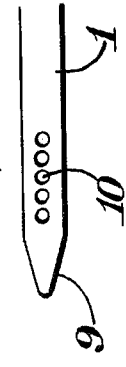
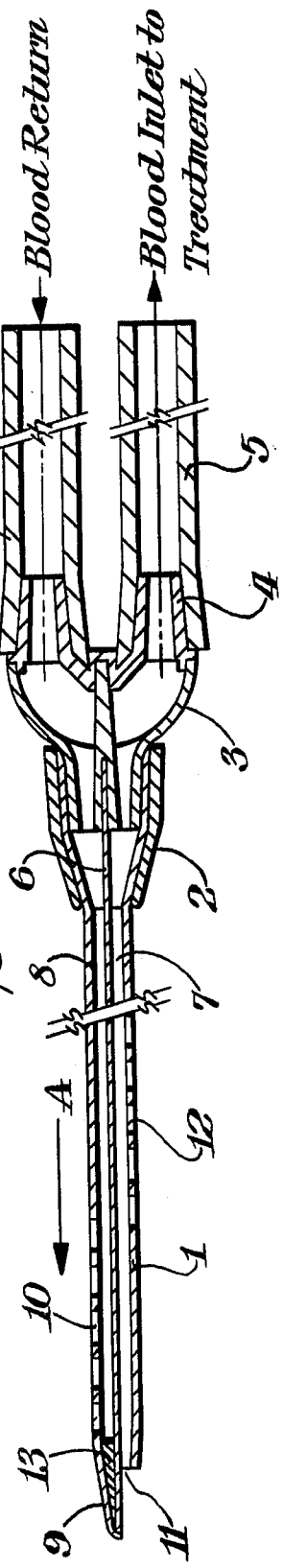

DUAL LUMEN SUBCLAVIAN CANNULA

BACKGROUND OF THE INVENTION

This invention relates to dual lumen cannulae for medical use, and more particularly for semipermanent means for simultaneously withdrawing blood from the subclavian vein for extra corporeal processing and returning the treated blood back to that vein at the same site.

Dual lumen cannulae have been proposed and used for hemodialysis because they provide the advantage of simultaneously withdrawing and returning blood of a patient through a single puncture rather than two. Such cannulae have been made of rigid metal tubes and are in general of two types: those with concentric flow lumens such as disclosed in U.S. Pat. No. 4,037,599 and those with parallel channels as in U.S. Pat. No. 4,203,436. These types are only suitable for a single blood treatment and must be emplaced in and removed from the patient for each use. None of them is flexible or suitable for emplacement in the subclavian vein. While these cannulas have proven useful, there would be an advantage for a cannula that can be left in place for several uses.

Single lumen cannulae suitable for semipermanent placement in the subclavian vein are known. These can be left in place for one to two weeks. One such type is the "Vas-Cath" subclavian cannula sold in the United States by Shiley Incorporated. These devices perform satisfactorily, but they require a more complex hemodialysis apparatus that must sequentially take in blood, treat it, return the treated blood to the patient. These steps cannot be done simultaneously as is most desirable.

SUMMARY OF THE INVENTION

This invention provides a dual lumen cannula suitable for semipermanent emplacement in a large blood vessel, such as the subclavian vein, to permit the continuous and simultaneous withdrawal, treatment and return of a patient's blood. It is especially useful for hemodialysis. The cannula can be kept in the body for a period of weeks, because it is made of a biocompatible plastic and is flexible enough to accommodate itself to bends in the vein without kinking. Also, the design minimizes the tendency for blood to clot in the cannula by reducing blood flow irregularities and other stagnant spots in the flow pattern.

The invention consists of a cannula assembly and a manifold assembly. The cannula assembly comprises a flexible tube divided into two blood flow lumens of approximately equal cross sectional area by an internal longitudinal septum. The distal end of the tube wall enclosing the second, or blood return, lumen is tapered to a closed blunt point against the septum. An opening is created in this return lumen by at least one hole in the tube wall just proximal to the tapered section. The distal end of the tube wall enclosing the first, or blood inlet, lumen is cut off to create an opening substantially normal to the septum and to the tube axis. This opening is located approximately opposite the proximal end of the tapered section of the second, lumen. An additional opening in the inlet lumen is created by at least one hole in the tube wall proximal to the openings in the second lumen. The proximal end of the cannula tube is connected to a manifold for separately collecting blood from the inlet and distributing blood to the return lumen.

It is the primary object of this invention to provide a dual lumen cannula, useful for hemodialysis, that can be implanted in a blood vessel of a patient and left in place for more than one treatment.

It is another object to provide a dual lumen cannula where distal inlet and return openings are sufficiently separated to avoid mixing of treated and untreated blood flows.

It is still another object to provide a dual lumen cannula in which blood clotting is inhibited.

BRIEF DESCRIPTION OF THE DRAWINGS

FIG. 1 is a longitudinal section view of one embodiment of the invention.

FIG. 2 shows the distal tip of the cannula viewed vertically down relative to FIG. 1.

FIG. 3 shows a cross section of the cannula tube.

FIG. 4 is a longitudinal section view of an alternative embodiment of the invention.

DESCRIPTION OF THE PREFERRED EMBODIMENTS

The components of a cannula according to this invention can be seen in FIG. 1. It is composed of the cannula tube 1, divided longitudinally by septum 6 to create two parallel lumens 7 and 8. Tube 1 is attached to a flow manifold assembly by locking ring 2. The manifold is composed of head unit 3 sealed to base 4. Locking ring 2 joins the cannula tube 1 securely to head 3, as by ultrasonic sealing. Conduits 5 are joint to base 4 by insertion into female fittings in base 4 to form liquid tight seals. These conduits carry blood in separate streams simultaneously back and forth between the manifold assembly and the extra corporeal blood processing unit, not shown. Arrow A indicates the direction of blood flow surrounding the cannula tube when it is properly emplaced in a vein. The proximal end of septum 6 is also sealed into head 3 to maintain separation of blood flow from the cannula tube lumens into the manifold. The first lumen 7 is usually the blood inlet lumen and is slightly shorter than the second lumen 8, usually the return lumen. A cross section of tube 1 is shown as FIG. 3.

The second lumen is closed at its distal end by tapering of the tube walls to a blunt point 9 against the septum. A distal opening is created for the second lumen by at least one hole, as 10, in the tube wall just proximal to the tapered section. The tapered distal tip of this second lumen can be filled with an insert substance, shown as 13 in FIGS. 1 and 4. FIG. 2 is a view of the distal end of the cannula tube and second lumen as seen when looking vertically downward relative to FIG. 1.

The tube wall forming the first lumen is cut off at a point approximately opposite the proximal end of the tapered section 9 of the second lumen to form a distal opening 11 approximately normal to both the septum and the tube axis. An additional opening for the second lumen is created by at least one hole, as 12, in the tube wall.

The blood carrying conduits 5 are composed of flexible blood compatible plastics such as silicone rubber or flexible vinyl tubing and usually lead to Luer fittings for convenient and secure connection to the blood treatment apparatus. The Luer fittings can be capped off when the cannula is not in use. These conduits are made flexible for convenience in closing them off by an occlusive clamp when it is desired.

FIG. 4 shows an alternative form of the cannula where the manifold base 4 provides male fittings for attaching the blood conduits 5.

Because the cannula tube will be semipermanently emplaced in a patient's blood vessel, the tube must be made of a material suitable for long exposure within the human body. It must have a relatively smooth surface and have a significantly less outside diameter than the inside diameter of the blood vessel selected for use. It must be flexible enough to follow and adapt to the natural curvature of the blood vessel and yet not kink on bending to constrict blood flow. The tube dimensions should very depending on patient size and the blood vessel used. However, in a preferred embodiment, suitable for the average adult subclavian vein, the tube and septum are made of flexible fluorinated ethylene propylene (FEP) resin, because of its good biocompatibility. This preferred cannula tube is of circular cross section and has the following dimensions: length about 200 mm; outside diameter about 4 mm; wall thickness about 0.6 mm; septum thickness about 0.6 mm. The distal holes creating openings in each lumen are preferably five 2 mm. diameter holes spaced about 1 mm apart. The preferred embodiment uses radio-opaque FEP resin to facilitate precise location of the distal cannula tip by X-ray observation.

The manifold parts and locking ring are preferably made of transparent polycarbonate plastic. The manifold is preferably made transparent to give visual indication of blood flow.

The design of this cannula minimizes blood clotting within the device during use by avoiding stagnant flow zones. In the prior art concentric tube dual lumen cannulas, the inner lumen tube unavoidedly comes in contact with the outer tube wall, especially when the cannula is bent. This creates zones, where the tube surfaces meet at acute angles, of relatively slow flowing blood. These stagnant areas promote clotting of the blood with attendant danger to the patient. The cannula of this invention avoids this problem because the cross section of the lumens contains no acute angles causing stagnant zones. Further, the cross section does not significantly change on bending. The tapered distal tip of the second lumen is preferably filled with inert plastic to eliminate that potentially stagnant zone.

The major flow of blood into the first lumen is through the side openings created by holes in the cannula tube wall. These holes are upstream of the blood return opening holes 10 in the second lumen when the cannula is properly emplaced in the vein, with the cannula tip pointing in the direction of blood flow as shown by arrow A in FIG. 1. Consequently, there is no recirculation of treated blood back into the inlet lumen.

The cannula is preferably emplaced with the help of a guide wire by the Seldinger technique. The principal use of the distal end opening of the first lumen is to facilitate this implantation. It permits the guide wire to pass freely through the cannula as the cannula slides into position over the wire. The distal tip is tapered to a blunt point to facilitate this entrance of the cannula into the body. The cannula, being flexible, will accommodate itself to any slight curvature in the vein. If desired, the cannula tube can be prebent by hand into an expected curve.

Once in place, this cannula can be left in the vein for several weeks. During this period, the patient does not have to be hospitalized. He can live a reasonably normal life with the cannula left in place between the two to three periods of active hemodialysis a week. An obvious advantage of this semi-permanent emplacement is that many fewer vein punctures are necessary, avoiding extensive scarring. Thus, useful vein sites for possible future and emergency use are preserved.

This invention has been described by reference to preferred embodiments and is not limited to such embodiments.

We claim:

1. A dual lumen subclavian cannula suitable for semi-permanent use, comprising:
    a flexible tube divided into first and second flow lumens by a flexible longitudinal septum, centrally located within said tube;
    the proximal end of said tube fitted to a manifold for separately collecting fluid from said first lumen and distributing fluid into said second lumen;
    the distal end of the tube wall enclosing said second lumen tapered to a closed blunt point at the axis of said septum, and provided with a distal opening by at least one aperture proximal to the tapered section of the tube wall;
    the distal end of the tube wall enclosing said first lumen extended to a position substantially opposite the proximal end of the tapered section of said second lumen and not closed, to provide a first distal opening for said first lumen; and
    a second distal opening for said first lumen provided by at least one aperture in the tube wall proximal to said distal opening in said second lumen.

2. A cannula according to claim 1 where the interior of said second lumen distal of its distal opening is filled with inert plastic.

3. A cannula according to claims 1 or 2 where the open areas provided by said at least one aperture in the tube wall enclosing each of said lumens total for each lumen at least the cross sectional area for flow of that lumen.

4. A cannula according to claims 1 or 2 where said at least one aperture in the tube walls enclosing each of said channels consists of five holes of diameter approximately equal to one-half the tubing internal diameter.

5. A cannula according to claims 1 or 2 where said tube and said septum are composed of radio-opaque fluorinated ethylene propylene.

6. A cannula according to claim 5 where said tube is of circular cross section.

* * * * *